United States Patent
Weigel et al.

(10) Patent No.: US 7,758,082 B2
(45) Date of Patent: Jul. 20, 2010

(54) FLUID LINE CONNECTOR SAFETY DEVICE

(75) Inventors: William Weigel, York, ME (US); Kenneth Everett Buckler, Methuen, MA (US); Jeffrey H Burbank, Boxford, MA (US); James M Brugger, Newburyport, MA (US); David Farias De Souza, Essex, MA (US)

(73) Assignee: NxStage Medical, Inc., Lawrence, MA (US)

( * ) Notice: Subject to any disclaimer, the term of this patent is extended or adjusted under 35 U.S.C. 154(b) by 152 days.

(21) Appl. No.: 11/951,142

(22) Filed: Dec. 5, 2007

(65) Prior Publication Data

US 2008/0129042 A1 Jun. 5, 2008

Related U.S. Application Data

(60) Provisional application No. 60/868,623, filed on Dec. 5, 2006.

(51) Int. Cl.
*F16L 55/00* (2006.01)
(52) U.S. Cl. ............................ 285/92; 285/81; 604/905; 604/241
(58) Field of Classification Search ................... 285/92, 285/81; 604/533, 905, 241
See application file for complete search history.

(56) References Cited

U.S. PATENT DOCUMENTS

| | | | | |
|---|---|---|---|---|
| 3,768,476 A | * | 10/1973 | Raitto | 604/326 |
| 3,874,713 A | * | 4/1975 | Myers | 285/340 |
| 4,045,058 A | * | 8/1977 | Eross | 285/119 |
| 4,230,109 A | * | 10/1980 | Geiss | 604/533 |
| 4,270,778 A | * | 6/1981 | Brownell | 285/305 |
| 4,340,052 A | * | 7/1982 | Dennehey et al. | 604/317 |
| 4,452,473 A | | 6/1984 | Ruschke | |
| 4,639,019 A | | 1/1987 | Mittleman | |
| 4,641,646 A | * | 2/1987 | Schultz et al. | 128/207.14 |
| 4,785,858 A | * | 11/1988 | Valentini et al. | 141/27 |
| 4,834,706 A | * | 5/1989 | Beck et al. | 604/111 |
| 4,950,255 A | * | 8/1990 | Brown et al. | 604/250 |
| 5,053,015 A | * | 10/1991 | Gross | 604/167.02 |
| 5,139,289 A | * | 8/1992 | Koss | 285/80 |
| 5,188,398 A | * | 2/1993 | Parimore et al. | 285/39 |
| 5,248,306 A | * | 9/1993 | Clark et al. | 285/114 |
| 5,350,201 A | * | 9/1994 | Bynum | 285/92 |
| 5,362,111 A | * | 11/1994 | Harbin | 285/92 |
| 5,490,693 A | * | 2/1996 | Fisher et al. | 285/92 |
| 5,620,427 A | * | 4/1997 | Werschmidt et al. | 604/535 |
| 5,984,373 A | | 11/1999 | Fitoussi et al. | |
| 6,213,996 B1 | * | 4/2001 | Jepson et al. | 604/533 |
| 6,217,564 B1 | * | 4/2001 | Peters et al. | 604/523 |
| 6,220,859 B1 | * | 4/2001 | Hoffman | 433/91 |
| 6,267,754 B1 | * | 7/2001 | Peters | 604/533 |
| 6,508,807 B1 | * | 1/2003 | Peters | 604/533 |
| 6,579,253 B1 | | 6/2003 | Burbank et al. | |
| 6,722,705 B2 | * | 4/2004 | Korkor | 285/332 |
| 6,893,056 B2 | * | 5/2005 | Guala | 285/332.1 |
| 7,156,424 B2 | * | 1/2007 | McCord | 285/92 |
| 7,347,458 B2 | * | 3/2008 | Rome et al. | 285/384 |
| 7,390,028 B2 | * | 6/2008 | Blazek | 285/317 |

* cited by examiner

*Primary Examiner*—David E Bochna
(74) *Attorney, Agent, or Firm*—Miles & Stockbridge P.C.; Mark A. Catan

(57) ABSTRACT

Devices having various features to prevent the disconnection of connectors used in medical treatments are disclosed. The devices can prevent disconnection of luer connectors that are incompletely mated.

2 Claims, 5 Drawing Sheets

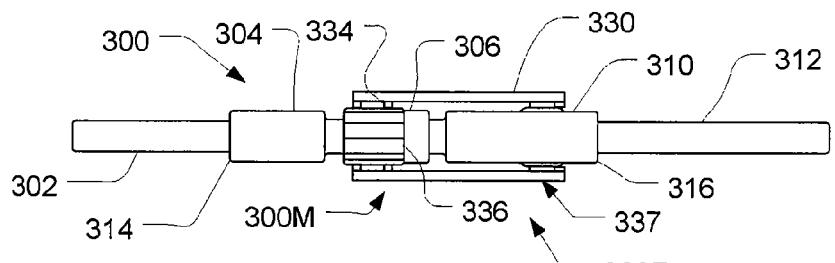
Fig. 10A
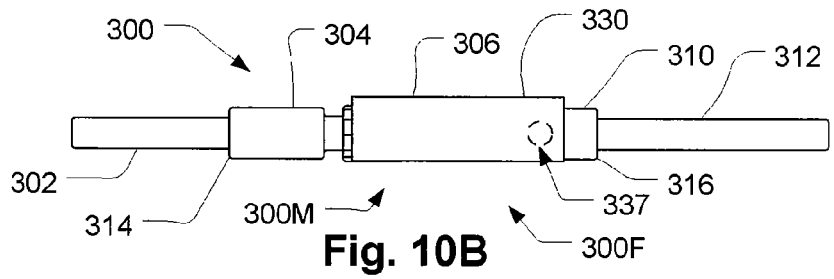
Fig. 10B
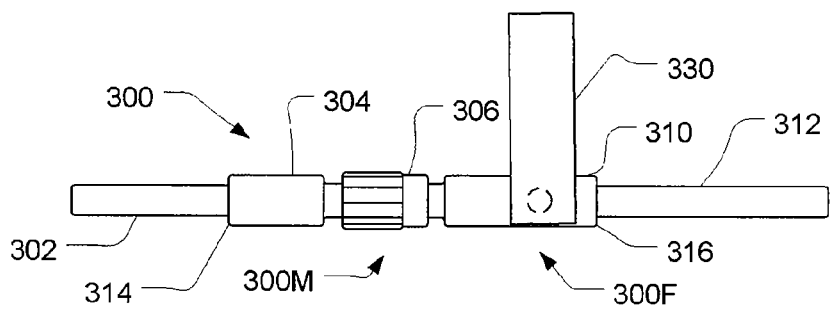
Fig. 10C
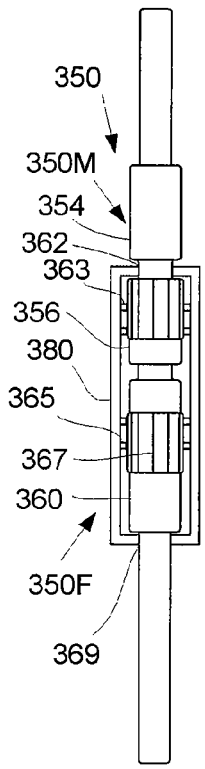
Fig. 10D
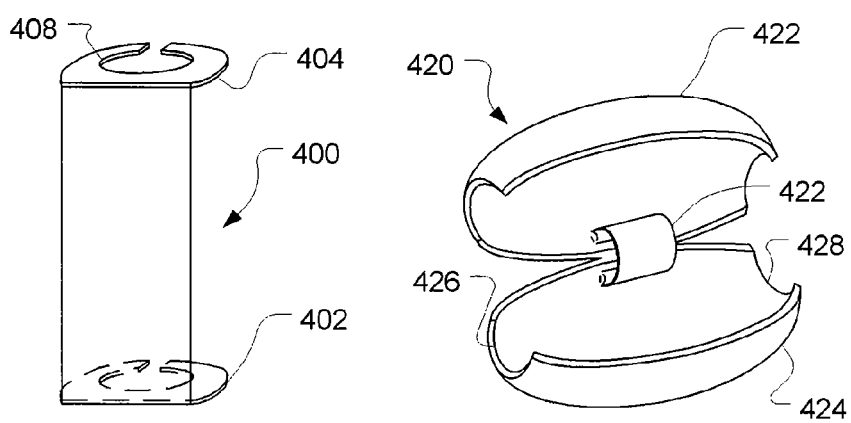
Fig. 11
Fig. 12
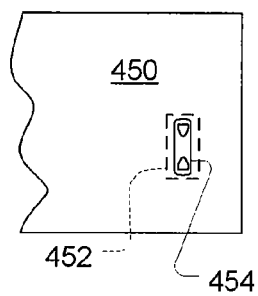
Fig. 13

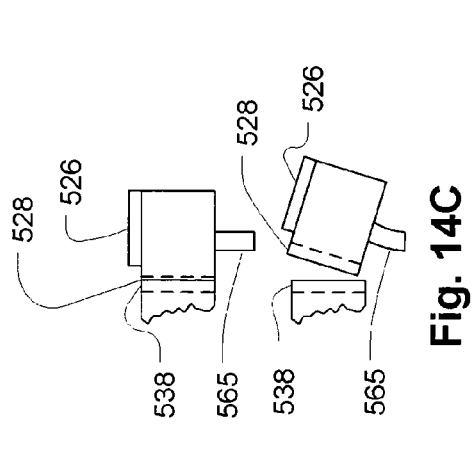
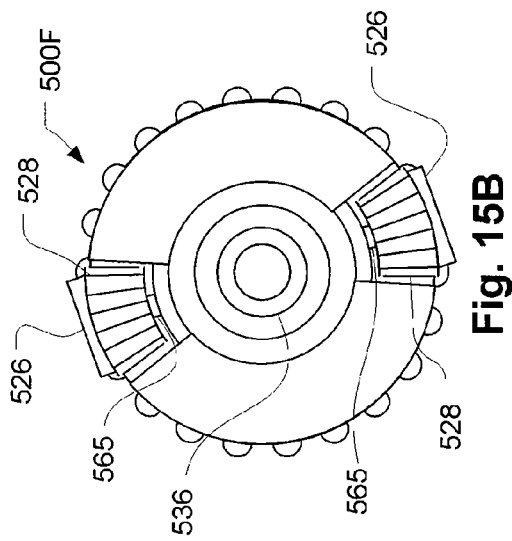
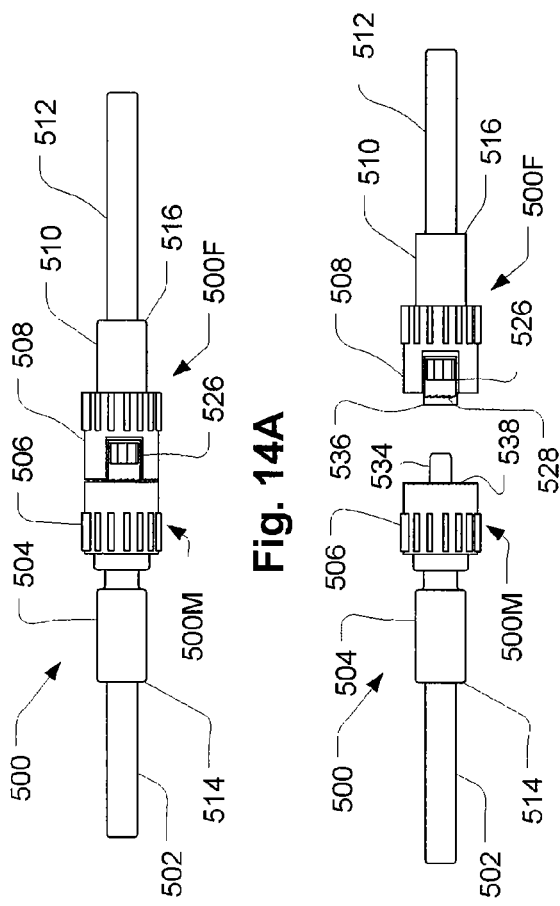

FLUID LINE CONNECTOR SAFETY DEVICE

FIELD OF THE INVENTION

The invention relates to fluid line connections and particularly to tubing connections such as those that are frequently employed in medical treatment devices.

BACKGROUND

Tubing connections are commonly used medical treatment systems, chemical processing plants, pharmaceutical plants, laboratories, etc. A common class of connectors mate by mutually rotating parts of the connectors, by pushing them together, or both. One common type of connector is a luer connector which includes a relatively long male element which fits tightly in a channel of a female element. In 1970s luers were merely pushed together to make a connection. Later, threaded collars were added to make it harder for the luer connectors to come apart. Even though the threaded collar increases the reliability of the connection, in some applications, such as extracorporeal blood treatment systems, it is desirable to address even minute levels of risk, if possible. There is a need in the art for simple and inexpensive ways to increase the reliability of connectors for fluid-carrying vessels and particularly, this need is felt in the area of tubing systems used in medical treatment devices. In particular, it would be desirable to enhance the security of luer-type connectors without altering the familiar features of their design or usability.

SUMMARY

Various mechanisms and methods for preventing the accidental decoupling of connectors are provided. All are particularly adapted for use with luer-type connectors.

According to an embodiment, a connector protection device operates with a connector having first and second mating parts which are held together by a non-frictional engagement device. The device includes a first connector and a second connector which are configured to mate to define a continuous flow path between them. A securing element prevents the first and second connectors disconnecting by at least one non-frictional mechanism. The securing element is movable with respect to at least one of the first and second connectors to allow the first and second connectors to disconnect. A disconnection prevention member extends between the first and second connectors and is effective to prevent at least one of a movement of the securing element and a separation of the first and second connectors such that the first and second connectors are prevented from disconnecting. In one variation, the first and second connectors form a luer-type connector and the securing element includes a threaded barrel on one of the first and second connectors that engages a threading element on the other of the first and second connectors. In a variation of the latter embodiment, the disconnection prevention member prevents the barrel from rotating relative to the other of the first and second connectors.

According to another embodiment, the connector protection device prevents the disengagement of two mating connectors which have a locking component that maintains the connection between the mating connectors by non-frictional means. For example, the two connectors may be screwed together or clamped together. Clamps and screws provide a positive engagement between the mating connectors. Whereas a luer connector without a locking thread portion, such as the prior art luer connectors lacking a locking device, relied on frictional engagement between the male and female luer to maintain the connection between the male and female connector components. In the embodiment, a protector helps to ensure that the connectors do not come apart either by backing the connector element up or by preventing it from disengaging and thereby permitting the connectors from coming apart. So, for example, if the connectors are luer connectors and the locking component is a threaded barrel, the connector protection device could serve the function defined by either preventing the barrel from rotating or by preventing the male and female luers from separating if the threaded barrel fails. Thus, in the embodiment, the connection protection device is one of: (1) a device that prevents the decoupling of the connectors such that failure of the connection is either prevented or inhibited by holding the connectors together and (2) a device that locks the locking component, thereby preventing it from failing to do its job.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIGS. 10A through 10C show a disconnect protector with a pivoting latch that prevents a threaded lock from rotating and, in a variation, also prevents the separation of the mating parts of the connector.

FIG. 10D shows a clip-on-type embodiment of a disconnect protector.

FIG. 11 shows a another clip-on type embodiment of a disconnect protector.

FIG. 12 shows a clam-shell embodiment of a disconnect protector.

FIG. 13 shows a portion of a medical tubing set support with an unused region that may be punched and formed to form one or more disconnect protectors.

FIGS. 14A through 14C show a disconnect protector that prevents rotation of a lock by a releasable ratchet mechanism.

FIGS. 15A and 15B show the ratchet mechanism of the embodiment of FIGS. 14A and 14B.

DETAILED DESCRIPTION OF THE EMBODIMENTS

Figure 1:
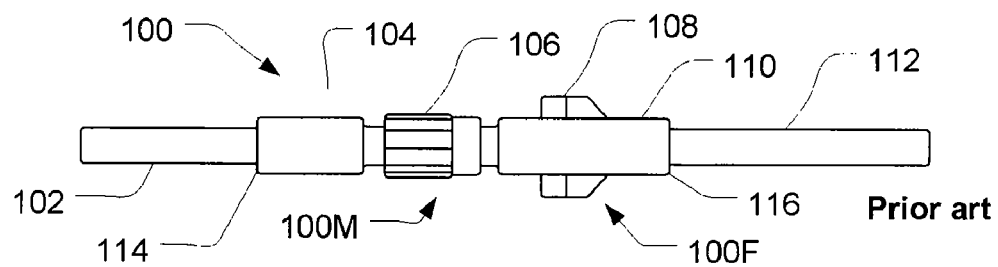
FIG. 1 shows a typical luer-type inline connector.

Referring to FIG. 1, a luer-type connector 100 has a male end 100M and a female end 100F. The male end 100M has an internally-threaded barrel 106 that threads with bosses or threads (not shown, but see, for example, U.S. Pat. No. 4,452,473 to Ruschke; U.S. Pat. No. 4,639,019 to Mittleman; and U.S. Pat. No. 5,984,373 to Fitoussi, et al, which are hereby incorporated by reference as fully set forth herein) on the female end 100F. The barrel 106 rotates relative to a male luer 104 (the conical mating portion of the connector is hidden within the barrel 106 and so is not shown, but is contiguous with the male luer 104) to engage the bosses or threads (again, not shown) to bring the female and male ends 100F and 100M together and force the male luer 104 into the female luer 110 (the conical recess that mates with the conical portion of the male luer 104 connector is hidden, partly within the barrel 106, and so is not shown, but is contiguous with the female luer 110). Note that in an alternative embodiment, the threaded barrel 106 could be on the female luer 110 and thread with bosses on the male luer 104 to similar effect. Tubes 102 and 112 together with the luer-type connector 100 form a continuous channel when the male and female luers 104 and 110 are mated. Wings 108 may be provided on one or both of the male and female luers 104 and 110.

Figure 2A:
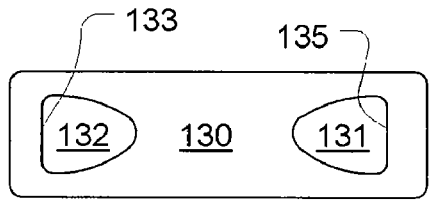
FIGS. 2A and 2B show a flexible disconnect protector design which prevents the luer-type connector of FIG. 1 from disconnecting.
Figure 2B:
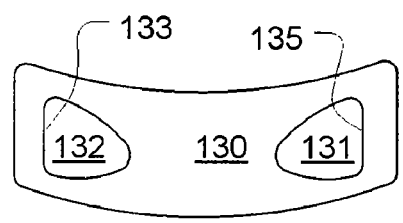
Figure 3:
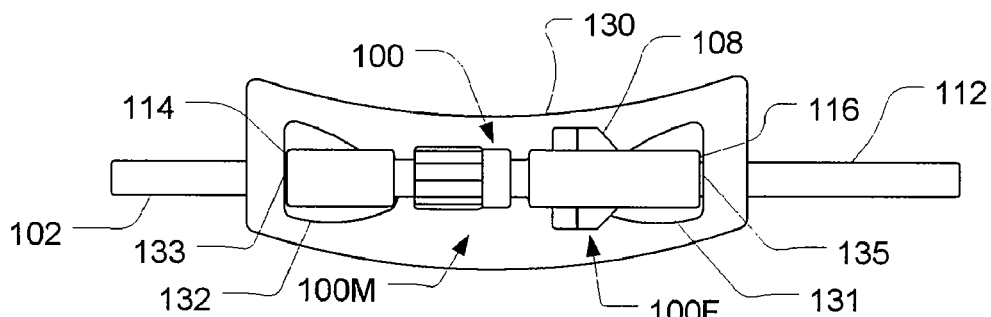
FIG. 3 shows the disconnect protector of FIGS. 2A and 2B positioned to prevent the disconnection of a luer-type connector.

Referring now also to FIGS. 2A, 2B and 3, edges 114 and 116 provide engagement portions for a disconnection protection device 130 which can be fitted over the mated luer-type connector 100 as shown in FIG. 3. The disconnection protection device 130, in the present embodiment, is of flexible material such as thermoplastic sheeting, steel, rubber, fiberglass or other composite, textile, or any suitable material that is resilient such that it can be bent as shown in FIG. 2B while springing back toward the relatively flat shape shown in FIG. 2A.

Figure 4:
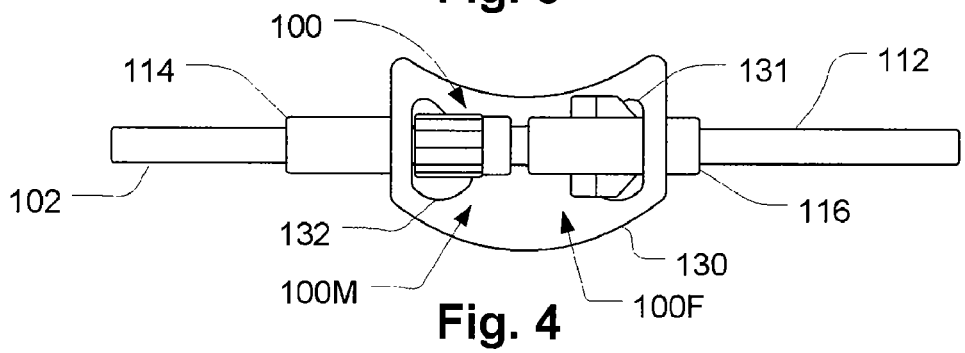
FIG. 4 illustrates a step and a configuration used to remove or install the disconnect protector of FIGS. 2A and 2B on the luer-type connector.
Figure 5:
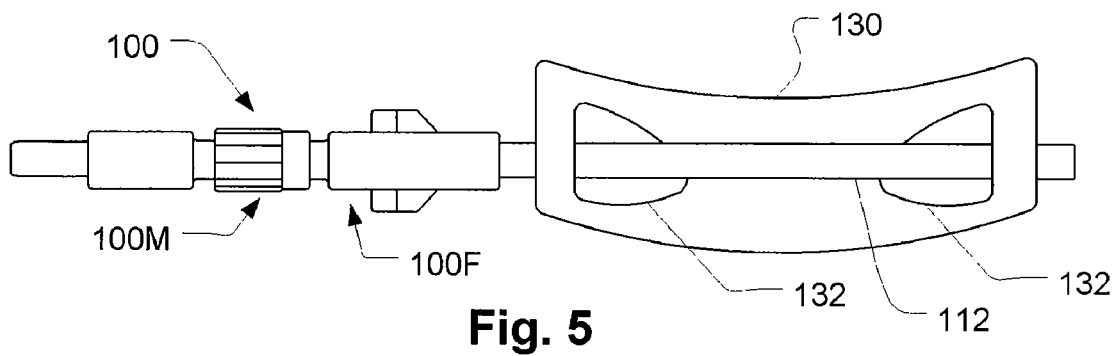
FIG. 5 shows a position in which the disconnect protector can be placed to disconnect the luer-type connector.

The disconnection protection device 130 can be moved over the luer-type connector 100 when bent as shown in FIG. 4 and when released in the position shown in FIG. 3, engages an edge 133 of opening 132 with the edge 114 and engages an edge 135 of opening 131 with the edge 116. Thus, in the position shown in FIG. 4, the disconnection protection device 130 prevents the male luer 104 and female luer 110 from moving apart. As a result, even if the barrel 106 is rotated to release the bosses or threads of the female end 100F, the male and female ends 100M and 100F will not come apart. The disconnection protection device 130 need not hold the male and female ends 100M and 100F tightly since the luer-type of connector forms a slowly-expanding channel as the male luer withdraws from of the female luer. As a result, a small amount of separation will produce a similarly small leak area and the male and female ends 100M and 100F must be drawn apart a considerable distance for a large leak to occur. As shown in FIG. 5, the disconnection protection device 130 can be bent and passed over one of the tubes 112 and 102 and released so that it remains in close proximity to the luer-type connector 100 while freeing the luer-type connector 100 to be closed or opened.

Figure 6:
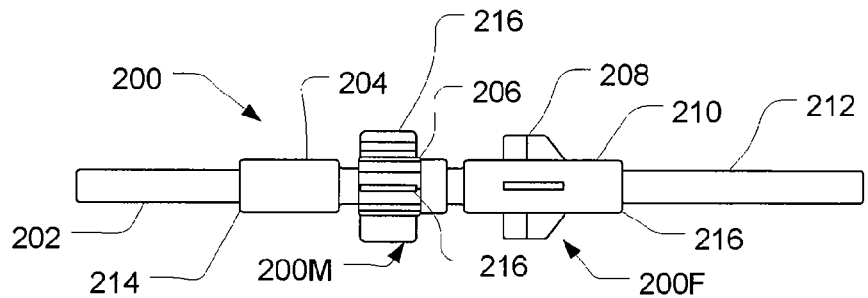
FIG. 6 shows a modified luer-type connector with wings on a rotating part that engage with another disconnect protector.

Referring to FIG. 6, a luer-type connector 200 has male a male end 200M and a female end 200F. The male end 200M has an internally-threaded barrel 206 that threads with bosses or threads (again, not shown but as described above and in the documents incorporated by reference) on the female end 200F. The barrel 206 rotates relative to a male luer 204 to engage the bosses or threads to bring the female and male ends 200F and 200M together and force the male luer 204 into the female luer 210. Note that in an alternative embodiment, the threaded barrel 206 could be on the female luer 210 and thread with bosses on the male luer 204 to similar effect. Tubes 202 and 212 together with the luer-type connector 200 form a continuous channel when the male and female luers 204 and 210 are mated. As in the above embodiments, wings 208 may be provided on one or both of the male and female luers 204 and 210.

Figure 7A:
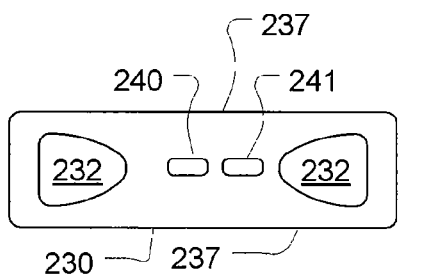
FIGS. 7A through 7C show additional embodiments of disconnect protector.
Figure 8:
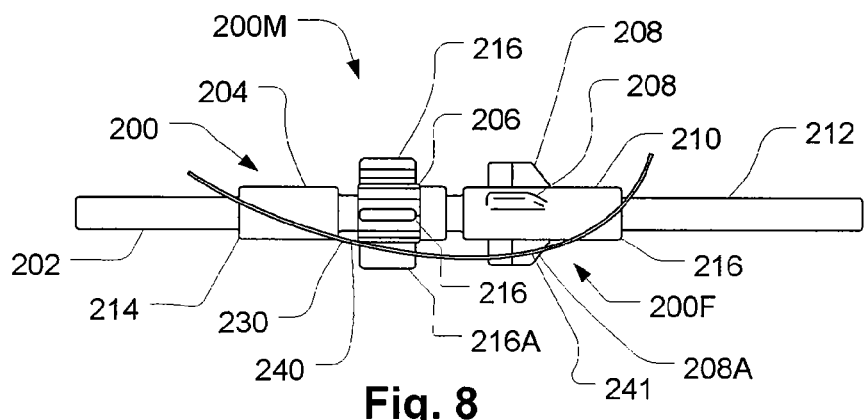
FIG. 8 shows the embodiment of FIG. 7A in use with the luer-type connector of FIG. 6.

In the embodiment of FIG. 6, extensions 216 are provided on the barrel 206. Also, there are four wings 208 on the female luer 210. Referring now also to FIGS. 7A and 8, a disconnection protection device 230 has openings 240 and 241 which receive one of the extensions 216 and one of the wings 208, respectively. As a result, when the disconnection protection device 230 is installed as discussed with reference to the embodiments of FIGS. 1-5, one extension 216A and one wing 208A fits through the openings 240 and 241, respectively thereby inhibiting the barrel 206 from rotating relative to the female luer 210. As a result, disconnection by unthreading the barrel internal threads from the female luer 210 bosses or threads is prevented.

Figure 7B:
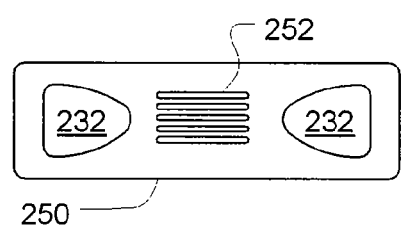
Figure 7C:
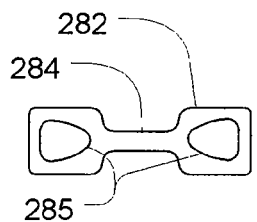

Referring to FIG. 7B, instead of openings 240 and 241, recesses 252 may be formed in a disconnection protection device 250 which is otherwise similar to that disconnection protection device 230 of FIG. 7A. The recesses 7B may be formed, for example, in thermoplastic sheeting, by molding, such as vacuum molding. Also, in alternative configurations, extensions 216 and wings 208 could be replaced by hook-shaped extensions that catch on or both of outer edges 237 of a device similar to the disconnection protection device 230. Also, alternatively, the disconnection protection device could have an hourglass shape as shown in FIG. 7C that necks down to create a narrow center section 284 between the openings 285 such that the extensions 216A wings 208A will catch the edge of the narrow center section 284.

Figure 9A:
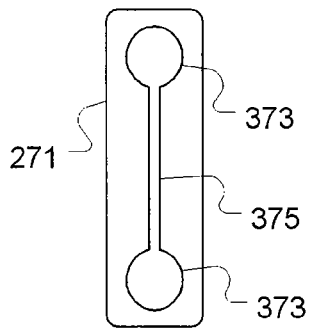
FIGS. 9A through 9C show various disconnect protectors.
Figure 9B:
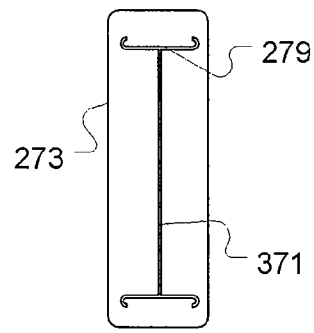
Figure 9C:
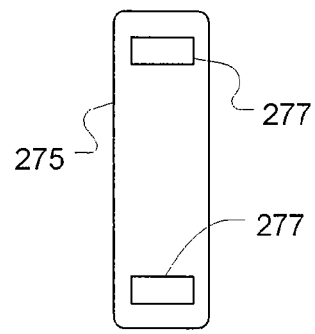

Referring to FIGS. 9A, 9B, and 9C, various alternative embodiments of disconnection protection device 271, 273, and 275 are shown. Disconnection protection device 271 has rounded openings 373, which is an alternative shape for the openings. The disconnection protection device 271 also has a bridging slot 375 which allows the disconnection protection device 271 to be snapped over the luer-type connector 100 or 200 rather than sliding it over the luer-type connector 100 or 200. Disconnection protection device 273 has slots 279 which are formed to allow them to expand to admit the luer-type connector 100 or 200 and a bridging slot 371 which allows the disconnection protection device 273 to be snapped over the luer-type connector 100 or 200. disconnection protection device 275 has rectangular openings 277.

Referring to FIG. 10A, a luer-type connector 300 has male a male end 300M and a female end 300F. The male end 300M has an internally-threaded barrel 306 that threads with bosses or threads (again, not shown but as described above and in the documents incorporated by reference) on the female end 300F. The barrel 306 rotates relative to a male luer 304 to engage the bosses or threads to bring the female and male ends 300F and 300M together and force the male luer 304 into the female luer 310. Again, note that in an alternative embodiment, the threaded barrel 306 could be on the female luer 310 and thread with bosses on the male luer 304 to similar effect. Tubes 302 and 312 together with the luer-type connector 300 form a continuous channel when the male and female luers 304 and 310 are mated.

Referring to FIGS. 10A through 10C, attached to the female luer 310 is a pivoting latch 330 that locks the barrel 306 to prevent it from rotating. The latch 330 pivots on a hinge 337 which holds the latch on the female luer 310. Protrusions 334 may be formed in the latch 330 to facilitated locking engagement of the barrel 305, which may be provided with a knurled surface 336. FIG. 10A shows the embodiment of the disconnection protection device 300 from a bottom perspective and FIG. 10B shows the same embodiment of the disconnection protection device 300 from the side. FIG. 10C shows the disconnection protection device 300 from the side with the latch 330 pivoted in a disengaged position to allow the barrel 306 to be rotated. The protrusions 334 may be shaped to cause the latch 330 to snap over the barrel 306, thereby holding the latch 330 in position as shown in FIGS. 10A and 10B. When engaged, the latch 330 prevents the barrel 306 from rotating relative to the female luer 310 thereby preventing the internal threads (not shown) of the barrel 306 from uncoupling from the bosses or threads (also not shown) of the female luer 310.

FIG. 10D shows a snap-on variation of a disconnection protection device 350 which snaps to both a male luer 354 barrel 356 and a female luer 360 which has a knurled surface 367. Protrusions 363 and 365 on a clip element 380 engage the knurled surface of the barrel 356 and the knurled surface 367 of the female luer 360. This prevents the barrel 356 from rotating relative to the female luer 360 thereby preventing disconnection by preventing the internal threads (not shown) of the barrel 356 from uncoupling from the bosses or threads (also not shown) of the female luer 360. The disconnection protection device 350 has narrow openings 362 and 369 that engage ends of the male luer 354 and the female luer 360 to prevent the male and female ends 350M and 350F from uncoupling even in the event the barrel 356 rotates or the threads are not engaged.

FIG. 11 shows another clip-on variation of a disconnection protection device 400 which has slots 408 in extensions 402 and 404 which engage the ends (for example, 214 and 216) to prevent the luer-type connector 100, 200 from decoupling. FIG. 12 shows a clamshell embodiment of a disconnection protection device 420 in which may be closed around the luer-type connector 100, 200 or similar connector. A curved leaf spring 422 closes the clamshell disconnection protection device 420 such that the covers 422 and 434 fully enclose the luer-type connector and such that the edges of the male and female luers (for example, 214 and 216) are held back while permitting the tubing to pass through openings 426 and 428. FIG. 13 shows a cartridge panel 450 which holds a tubing set which may include one or more luer-type connectors. The cartridge panel 450 may be made of sheet material whose properties are suitable for some of the disconnection protection devices described herein. The cartridge panel may have various cutouts and other shapes formed in it in various operations such as punching and vacuum-forming. An unused area is shown at 452 and the outline of a disconnection protection device 454 is shown. In the embodiment, the disconnection protection device 454 is formed and cut from the cartridge panel 450 during its manufacture. The cartridge panel is described in U.S. Pat. No. 6,579,253 to Burbank, et al, hereby incorporated by reference as if fully set forth herein.

Referring to FIGS. 14A and 14B, a luer-type connector 500 has male a male end 500M and a female end 500F. The male end 500M has an internally-threaded barrel 506 that threads with bosses or threads (again, not shown but as described above and in the documents incorporated by reference) on the female end 500F. The barrel 506 rotates relative to a male luer 504 to engage the bosses or threads to bring the female and male ends 500F and 500M together and force the male luer 504 into the female luer 510. Again, note that in an alternative embodiment, the threaded barrel 506 could be on the female luer 510 and thread with bosses on the male luer 504 to similar effect. Tubes 502 and 512 together with the luer-type connector 300 form a continuous channel when the male and female luers 304 and 310 are mated. FIG. 14B, which shows the luer-type connector 500 uncoupled, shows a tapered end 534 of the male luer 504 and an end 536 of the female luer 510 which has the mating conical recess that receives the male luer 504 tapered end 534.

The luer-type connector 500 has a disconnection protection device integrated in the design of the connector. On the female luer 510, a ratchet barrel 508 has a ratchet 526 with teeth 528 which is urged toward a circular rack 538 by a living hinge 565. The teeth of both the rack 538 and ratchet 526 are shaped to cause them to engage such that the barrel 506 cannot turn relative to the ratchet 526 of the female luer 510, thereby preventing unthreading. This is similar to the well-known structure of cable ties, typically made of nylon. As shown in FIG. 14C, the living hinge 565 allows pressure to be applied to the top of the ratchet 526 by squeezing or pinching the ratchet barrel 508. This causes the ratchet surface 528 to withdraw from the circular rack 538 disengaging the barrel 506 allowing the luer-type connector 500 to be uncoupled. In this embodiment, as in the others, the ratchet could be provided on the male end and the rack on the female end of the luer-type connector with similar effect. This is true in all of the above embodiments, whether specifically indicated with respect to the embodiment or not.

In an embodiment, the connector protection device prevents the disengagement of two mating connectors which have a locking component that maintains the connection between the mating connectors by non-frictional means. For example, the two connectors may be screwed together or clamped together. Clamps and screws provide a positive engagement between the mating connectors. Whereas a luer connector without a locking thread portion, such as the prior art luer connectors lacking a locking device, relied on frictional engagement between the male and female luer to maintain the connection between the male and female connector components. In the embodiment, a protector helps to ensure that the connectors do not come apart either by backing the connector element up or by preventing it from disengaging and thereby permitting the connectors from coming apart. So, for example, if the connectors are luer connectors and the locking component is a threaded barrel, the connector protection device could serve the function defined by either preventing the barrel from rotating or by preventing the male and female luers from separating if the threaded barrel fails. Thus, in the embodiment, the connection protection device is one or both of: (1) a device that prevents the decoupling of the connectors such that failure of the connection is either prevented or inhibited by holding the connectors together and (2) a device that locks the locking component, thereby preventing it from failing to do its job.

In the embodiment of FIGS. 1 through 5, the locking element is the barrel 106 and the connector protection element is the disconnection protection device 130. The disconnection protection device 130 falls into the first category; that is, it prevents the decoupling of the connectors (male luer 104 and female luer 110) such that failure of the connection is either prevented or inhibited by holding the connectors together embodiment.

In the embodiments of FIGS. 9A through 9C, the disconnection protection devices 271, 273, and 275 perform the same role. In the embodiments of FIGS. 6 through 8, the disconnection protection devices 230 and 250 also perform the same role of preventing the decoupling of the connectors (male luer 204 and female luer 210) such that failure of the connection is either prevented or inhibited by holding the connectors together but they also serve the second role of locking the locking component (i.e., the barrel 206), thereby preventing the barrel 216 from failing to do its job.

In the example of the embodiment of FIGS. 6 through 8, the barrel 206 is prevented from rotating relative to the female luer 210 by causing the extension 216 and the wing of the female luer 210 from engaging a common element, namely the disconnection protection device 230. This in turn prevents relative rotation of the female luer 210 and the barrel 206 thereby preventing disengagement of the barrel threads from the female luer bosses or threads.

In the embodiment of FIGS. 10A through 10C, the locking element is the barrel 306 and the connector protection element is the latch 330. The disconnection protection device 330 falls into the second category; that is, it locks the locking component (the barrel 306), thereby preventing it from failing to do its job of holding the threaded elements in continuous engagement to keep the male and female luers 304 and 310 mated. The embodiment of FIG. 10D is similar to the embodiment of FIG. 10A in that the locking element, the barrel 356 is prevented from rotating. But in this case, the disconnection protection device 352 also prevents the separation of the male and female luers 354 and 360. Thus, the disconnection protection device 350 falls into both categories 1 and 2.

In the disconnection protection device 500 of FIGS. 14A through 15B, the locking element is the barrel 506 and the connection protection element is the ratchet 526. The disconnection protection device 500 thus fits in category 2 because it prevents the barrel 506 from disengaging with the female luer 510.

In an embodiment of the invention, the connectors are luer connectors. In another, or a refinement of any of the foregoing embodiments, the connectors are used to secure a line of a medical treatment device. In yet another, or a refinement of any of the foregoing embodiments, the connectors connect blood-conveying lines of a medical treatment device. In another, or a refinement of any of the foregoing embodiments, the locking element includes a ratchet. In a further refinement, it includes rack that is engageable with the ratchet. In yet another, or a refinement of any of the foregoing embodiments, the connectors are male and female luers and the locking element includes a threaded barrel on either the male or female luer that engages on a mating portion of the other of the male and female luer.

Figure 16A:
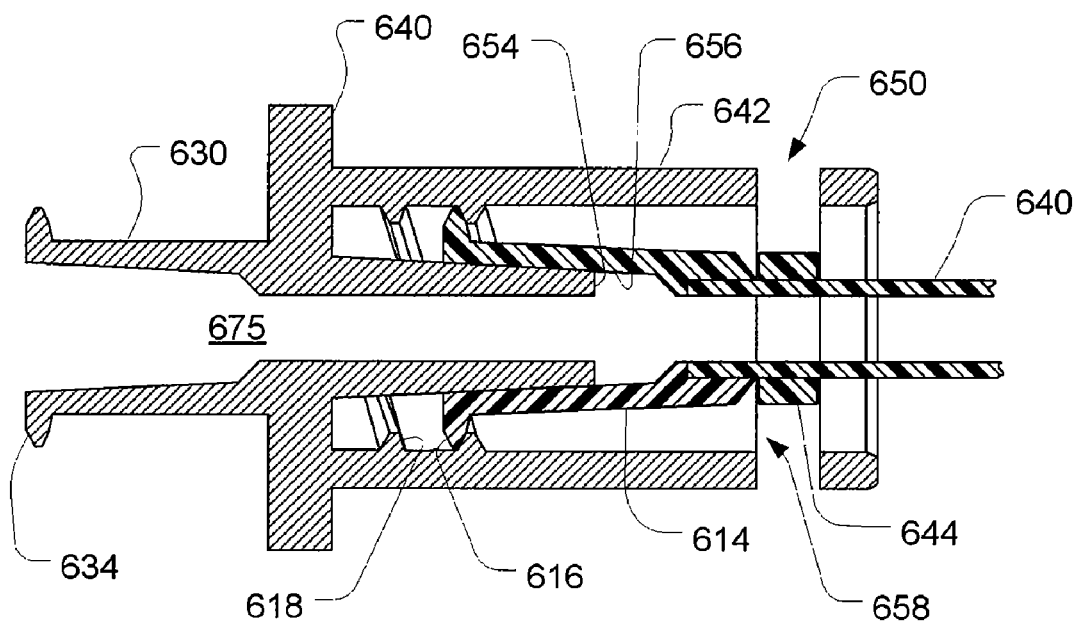
FIGS. 16A and 16B show an adapter that can be added to a connector that lacks an appropriately-shaped portion with an edge to engage the disconnection protection device of the embodiments of FIG. 2A, for example.
Figure 16B:
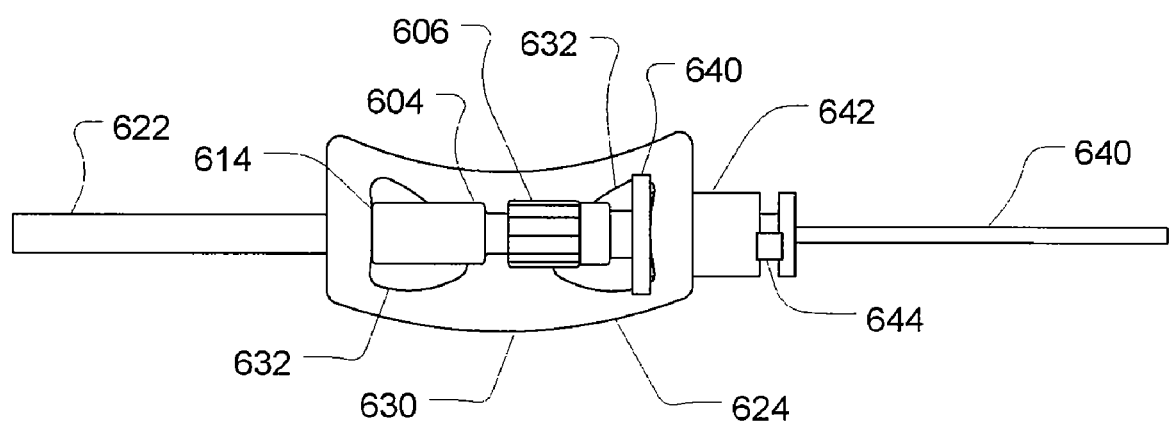

FIGS. 16A and 16B show an adapter that can be added to connector components that do not have an edge that can securely engage the disconnection protection device of FIG. 2A, for example. A connector 614, in this case a female luer which is secured to a catheter 640 has tabs 616 that engage threads of standard locking male luer connectors. A connector adapter 642 has a male luer with a recess 658 that has threads 618 to engage the tabs 616 in precisely the manner of a standard locking male luer connector. Integrally formed in the connector adapter 642 is a connector 630, that replicates the original connector 614, in this case, a female luer. When threaded onto the original connector 614, the connector adapter defines a continuous channel from the connector 630 to the original connector 614. The connector adapter 642 is additionally fastened to the connector 614 by a flexible band that is received in recesses 650 such that it wraps tightly to the diameter of the catheter 640. Thus, the connector 614 is held in the recess 658 such that even if the it disengages from the threads 618, it cannot withdraw from the connector adapter 642.

The connector adapter 642 provides a flange 640 that can engage the disconnect protection device 624. In the example shown in FIG. 16B, a male luer 604 with a threaded barrel 606 is connected to the female luer 630 of the connector adapter 642. The disconnection protection device 630 is engages the flange 640 and the male luer 604 edge 614 thereby preventing the disconnection of the catheter 640 from a fluid line 622.

In any of the above embodiments, the type of connector could be luer-type connector or any other connector which rely on mutually rotatable parts on the connecting elements or which slide apart to disconnect or both. Also, although inline connectors are shown for purposes of illustration, the disconnect protection features shown can be applied to other types of connectors such as connectors forming parts of junctions, other components such as valves or filters, and others.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

The invention claimed is:

1. A connection device, comprising:
a male luer and a female luer, the female luer having a wing extending axially along the female luer and protruding radially from the female luer;
a threaded luer lock configured to prevent the male and female luers from separating; and
a flexible disconnection prevention device having an opening formed therein, the flexible disconnection prevention device being configured to prevent the luer lock from rotating when the wing of the female luer is positioned in the opening of the disconnection prevention device, or to prevent the male and female luers from separating in the event the luer lock rotates.

2. The device of claim 1, wherein the opening of the disconnection prevention device is configured to engage the male luer such that the male luer and female luer are prevented from separating.

* * * * *